(12) United States Patent
Deisseroth et al.

(10) Patent No.: US 8,398,692 B2
(45) Date of Patent: Mar. 19, 2013

(54) SYSTEM FOR OPTICAL STIMULATION OF TARGET CELLS

(75) Inventors: Karl Deisseroth, Palo Alto, CA (US); Feng Zhang, Cambridge, MA (US); Edward Boyden, Cambridge, MA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 630 days.

(21) Appl. No.: 12/522,520

(22) PCT Filed: Jan. 10, 2008

(86) PCT No.: PCT/US2008/050745
§ 371 (c)(1), (2), (4) Date: Jan. 8, 2010

(87) PCT Pub. No.: WO2008/086470
PCT Pub. Date: Jul. 18, 2008

(65) Prior Publication Data
US 2010/0145418 A1     Jun. 10, 2010

Related U.S. Application Data

(60) Provisional application No. 60/879,669, filed on Jan. 10, 2007, provisional application No. 60/903,248, filed on Feb. 23, 2007.

(51) Int. Cl.
*A61N 5/06*     (2006.01)
(52) U.S. Cl. ........................................................ 607/88
(58) Field of Classification Search ............... 435/173.1, 435/289.1; 604/20; 607/2, 92, 88
See application file for complete search history.

(56) References Cited

U.S. PATENT DOCUMENTS

| | | | |
|---|---|---|---|
| 2,968,302 | A | 1/1961 | Fry et al. |
| 3,499,437 | A | 3/1970 | Balamuth et al. |
| 3,567,847 | A | 3/1971 | Applegrove Circle et al. |
| 4,343,301 | A | 8/1982 | Indech |
| 4,559,951 | A | 12/1985 | Dahl et al. |
| 4,616,231 | A | 10/1986 | Autrey et al. |
| 4,865,042 | A | 9/1989 | Umemura et al. |
| 4,879,284 | A | 11/1989 | Land et al. |
| 5,032,123 | A | 7/1991 | Katz et al. |
| 5,041,224 | A | 8/1991 | Ohyama et al. |

(Continued)

FOREIGN PATENT DOCUMENTS

| EP | 1 334 748 | 8/2003 |
|---|---|---|
| JP | 06-295350 | 10/1994 |

(Continued)

OTHER PUBLICATIONS

Aebischer, et al. "Long-Term Cross-Species Brain Transplantation of a Polymer-Encapsulated Dopamine-Secreting Cell Line", Experimental Neurology, 1991, vol. 111, pp. 269-275.

(Continued)

*Primary Examiner* — Jessica Stultz
*Assistant Examiner* — Tuan Nguyen
(74) *Attorney, Agent, or Firm* — Paula A. Borden; Bozicevic, Field & Francis LLP.

(57) ABSTRACT

Various systems and methods are implemented for controlling stimulus of a cell. One such method is implemented for optical stimulation of a cell expressing an NpHR ion pump. The method includes the step of providing a sequence of stimuli to the cell. Each stimulus increases the probability of depolarization events occurring in the cell. Light is provided to the cell to activate the expressed NpHR ion pump, thereby decreasing the probability of depolarization events occurring in the cell.

10 Claims, 4 Drawing Sheets

U.S. PATENT DOCUMENTS

| | | |
|---|---|---|
| 5,082,670 A | 1/1992 | Gage et al. |
| 5,249,575 A | 10/1993 | Di Mino et al. |
| 5,460,950 A | 10/1995 | Barr et al. |
| 5,460,954 A | 10/1995 | Lee et al. |
| 5,470,307 A | 11/1995 | Lindall |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,738,625 A | 4/1998 | Gluck |
| 5,739,273 A | 4/1998 | Engelman et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,939,320 A | 8/1999 | Littman et al. |
| 6,134,474 A | 10/2000 | Fischell et al. |
| 6,161,045 A | 12/2000 | Fischell et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,597,954 B1 | 7/2003 | Pless et al. |
| 6,609,020 B2 | 8/2003 | Gill |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,313,442 B2 | 12/2007 | Velasco et al. |
| 7,603,174 B2 | 10/2009 | De Ridder |
| 7,613,520 B2 | 11/2009 | De Ridder |
| 2002/0094516 A1 | 7/2002 | Calos et al. |
| 2002/0155173 A1 | 10/2002 | Chopp et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0104512 A1 | 6/2003 | Freeman et al. |
| 2003/0204135 A1 | 10/2003 | Bystritsky |
| 2003/0232339 A1 | 12/2003 | Shu et al. |
| 2004/0039312 A1 | 2/2004 | Hillstead et al. |
| 2004/0122475 A1 | 6/2004 | Myrick et al. |
| 2004/0203152 A1 | 10/2004 | Calos |
| 2005/0058987 A1 | 3/2005 | Shi et al. |
| 2005/0119315 A1 | 6/2005 | Fedida et al. |
| 2005/0124897 A1 | 6/2005 | Chopra |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0155348 A1 | 7/2006 | De Charms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0216689 A1 | 9/2006 | Maher et al. |
| 2006/0236525 A1 | 10/2006 | Sliwa et al. |
| 2006/0271024 A1 | 11/2006 | Gertner et al. |
| 2007/0053996 A1 | 3/2007 | Boyden et al. |
| 2007/0054319 A1 | 3/2007 | Deisseroth et al. |
| 2007/0060915 A1 | 3/2007 | Kucklick |
| 2007/0135875 A1 | 6/2007 | Demarais et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0261127 A1 | 11/2007 | Boyden et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0077200 A1 | 3/2008 | Bendett et al. |
| 2008/0085265 A1* | 4/2008 | Schneider et al. ......... 424/93.21 |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2009/0054954 A1 | 2/2009 | Foley et al. |
| 2009/0088680 A1 | 4/2009 | Aravanis et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0254134 A1 | 10/2009 | Nikolov et al. |
| 2010/0009444 A1 | 1/2010 | Herlitze et al. |
| 2010/0190229 A1 | 7/2010 | Zhang et al. |
| 2010/0234273 A1 | 9/2010 | Boyden et al. |
| 2011/0105998 A1 | 5/2011 | Deisseroth et al. |
| 2011/0112179 A1 | 5/2011 | Deisseroth et al. |
| 2011/0159562 A1 | 6/2011 | Deisseroth et al. |
| 2011/0166632 A1 | 7/2011 | Deisseroth et al. |
| 2011/0172653 A1 | 7/2011 | Deisseroth et al. |
| 2011/0301529 A1 | 12/2011 | Zhang et al. |
| 2011/0311489 A1 | 12/2011 | Deisseroth et al. |

FOREIGN PATENT DOCUMENTS

| | | |
|---|---|---|
| WO | WO 01-25466 | 4/2001 |
| WO | WO 03-040323 | 5/2003 |
| WO | WO 03-084994 | 10/2003 |
| WO | WO 03-102156 | 12/2003 |
| WO | WO 2007-024391 | 3/2007 |
| WO | WO 2007-131180 | 11/2007 |
| WO | WO 2009-131837 | 10/2009 |

OTHER PUBLICATIONS

Ahmad, et al. "The *Drosophila rhodopsin* cytoplasmic tail domain is required for maintenance of rhabdomere structure." The FASEB Journal, 2007, vol. 21, p. 449-455.

Akirav, et al. "The role of the medial prefrontal cortex-amygdala circuit in stress effects on the extinction of fear", Neural Plasticity, 2007: vol. 2007 Article ID:30873, pp. 1-11.

Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.

Araki, et al. "Site-Directed Integration of the *cre* Gene Mediated by Cre Recombinase Using a Combination of Mutant *lox* Sites", Nucleic Acids Research, 2002, vol. 30, No. 19, pp. 1-8.

Aravanis, et al. "An optical neural interface: in vivo control of rodent motor cortex with integrated fiberoptic and optogenetic technology," J. Neural. Eng., 2007, vol. 4(3):S143-S156.

Argos, et al. "The integrase family of site-specific recombinases: regional similarities and global diversity", The EMBO Journal, 1986, vol. 5, No. 2, pp. 433-440.

Banghart, et al. "Light-activated ion channels for remote control of neuronal firing". Nature Neuroscience, 2004, vol. 7, No. 12 pp. 1381-1386.

Basil et al. "Is There Evidence for Effectiveness of Transcranial Magnetic Stimulation in the Treatment of Psychiatric Disorders?" Psychiatry, 2005, pp. 64-69.

Bebbington et al., "The use of vectors based on gene amplification for the expression of cloned genes in mammalian cells in DNA cloning" vol. 3, Academic Press, New York, 1987.

Benabid "Future strategies to restore brain functions," Conference proceedings from Medicine Meets Millennium: World Congress of Medicine and Health, 2000, 6 pages.

Benoist et al. "In vivo sequence requirements of the SV40 early promotor region" Nature (London), 1981, vol. 290(5804): pp. 304-310.

Berges et al., "Transduction of Brain by Herpes Simplex Virus Vectors", Molecular Therapy, 2007, vol. 15, No. 1: pp. 20-29.

Berridge et al., "The Versatility and Universality of Calcium Signaling", Nature Reviews: Molecular Cell Biology, 2000, vol. 1: pp. 11-21.

Boyden, et al. "Millisecond-timescale, genetically targeted optical control of neural activity" Nature Neuroscience, 2005, vol. 8, No. 9: pp. 1263-1268.

Bi, et al. "Ectopic Expression of a Microbial-Type Rhodopsin Restores Visual Responses in Mice with Photoreceptor Degeneration", Neuron, 2006, vol. 50, No. 1: pp. 23-33.

Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.

Blomer et al., "Highly Efficient and Sustained Gene Transfer in Adult Neurons with Lentivirus Vector", Journal of Virology,1997, vol. 71, No. 9: pp. 6641-6649.

Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-7.

Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.

Brown, et al. "Long-term potentiation induced by θ frequency stimulation is regulated by a protein phosphate-coupled gate." The Journal of Neuroscience, 2000, vol. 20, No. 21, pp. 7880-7887.

Callaway, et al. "Photostimulation using caged glutamate reveals functional circuitry in living brain slices", Proc. Natl. Acad. Sci. USA., 1993, vol. 90: pp. 7661-7665.

Cenatiempo "Prokaryotic gene expression in vitro: transcription-translation coupled systems", Biochimie, 1986, vol. 68(4): pp. 505-515.

Claudio et al. "Nucleotide and deduced amino acid sequences of *Torpedo californica* acetylcholine receptor gamma subunit." PNAS USA,1983, vol. 80, p. 1111-1115.

Collingridge et al. "Inhibitory post-synaptic currents in rat hippocampal CA1 neurones." J. Physiol., 1984, vol. 356, pp. 551-564.

Covington, et al. "Antidepressant Effect of Optogenetic Stimulation of the Medial Prefrontal Cortex." Journal of Neuroscience, 2010, vol. 30(48), pp. 16082-16090.

Crouse, et al. "Expression and amplification of engineered mouse dihydrofolate reductase minigenes" Mol. Cell. Biol. , 1983, vol. 3(2): pp. 257-266.

Cucchiaro et al., "*Phaseolus vulgaris* leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.

Cucchiaro et al., "Electron-Microsoft Analysis of Synaptic Input from the Perigeniculate Nucleus to A-Lamine of the Lateral Geniculate Nucleus in Cats", The Journal of Comparitive Neurology, 1991, vol. 310, pp. 316-336.

Cui, et al., "Electrochemical deposition and characterization of conducting polymer polypyrrole/PSS on multichannel neural probes," Sensors and Actuators, 2001, vol. 93(1): pp. 8-18.

Date, et al. "Grafting of Encapsulated Dopamine-Secreting Cells in Parkinson's Disease: Long-Term Primate Study", Cell Transplant, 2000, vol. 9, pp. 705-709.

Dalva, et al. "Rearrangements of Synaptic Connections in Visual Cortex Revealed by Laser Photostimulation", Science, 1994,vol. 265, pp. 255-258.

Dederen, et al. "Retrograde neuronal tracing with cholera toxin B subunit: comparison of three different visualization methods", Histochemical Journal, 1994, vol. 26, pp. 856-862.

Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.

Deisseroth et al., "Translocation of Calmodulin to the Nucleus Supports CREB Phosphorylation in Hippocampal Neurons", Nature, 1998, vol. 392, pp. 198-202.

Deisseroth et al., "Signaling from Synapse to Nucleus: the logic Behind the Mechanisms", Currrent Opinion in Neurobiology, 2003, vol. 13, pp. 354-365.

Deisseroth "Next-generation optical technologies for illuminating genetically targeted brain circuits," The Journal of Neuroscience, 2006, vol. 26, No. 41, pp. 10380-10386.

Denk, W., et al. "Anatomical and functional imaging of neurons using 2-photon laser scanning microscopy", Journal of Neuroscience Methods, 1994, vol. 54, pp. 151-162.

Ditterich, et al. "Microstimulation of visual cortex affects the speed of perceptual decisions", 2003, Nature Neuroscience, vol. 6, No. 8, pp. 891-898.

Dittgen, et al. "Lentivirus-based genetic manipulations of cortical neurons and their optical and electrophysiological monitoring in vivo", PNAS, 2004, vol. 101, No. 52, pp. 18206-18211.

Eisen, "Treatment of amyotrophic lateral sclerosis", Drugs Aging, 1999; vol. 14, No. 3, pp. 173-96.

Esposito et al. "The integrase family of tyrosine recombinases: evolution of a conserved active site domain" , Nucleic Acids Research, 1997, vol. 25, No. 18, pp. 3605-3614.

Evanko "Optical excitation yin and yang" Nature Methods, 2007, 4:384.

Fabian et al. "Transneuronal transport of lectins" Brain Research, 1985, vol. 344, pp. 41-48.

Falconer et al. "High-throughput screening for ion channel modulators," Journal of Biomolecular Screening, 2002, vol. 7, No. 5, pp. 460-465.

Farber, et al. "Identification of Presynaptic Neurons by Laser Photostimulation", Science, 1983, vol. 222, pp. 1025-1027.

Feng, et al. "Imaging Neuronal Subsets in Transgenic Mice Expressing Multiple Spectral Variants of GFP", Neuron, 2000, vol. 28, pp. 41-51.

Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.

Fitzsimons et al., "Promotors and Regulatory Elements that Improve Adeno-Associated Virus Transgene Expression in the Brain", 2002, Methods, vol. 28, pp. 227-236.

Foster, "Bright blue times", Nature, 2005, vol. 433, pp. 698-699.

Gelvich et al. "Contact flexible microstrip applicators (CFMA) in a range from microwaves up to short waves," IEEE Transactions on Biomedical Engineering, 2002, vol. 49, Issue 9: 1015-1023.

Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.

Gilman, et al. "Isolation of sigma-28-specific promoters from *Bacillus subtilis* DNA" Gene, 1984, vol. 32(1-2): pp. 11-20.

Glick et al."Factors affecting the expression of foreign proteins in *Escherichia coli*", Journal of Industrial Microbiology, 1987, vol. 1(5): pp. 277-282.

Goekoop, R. et al. "Cholinergic challenge in Alzheimer patients and mild cognitive impairment differentially affects hippocampal activation—a pharmacological fMRI study." Brain, 2006, vol. 129, pp. 141-157.

Gordon, et al. "Regulation of Thy-1 Gene Expression in Transgenic Mice", Cell, 1987, vol. 50, pp. 445-452.

Gorelova et al., "The course of neural projection from the prefrontal cortex to the nucleus accumbens in the rat", Neuroscience, 1997, vol. 76, No. 3, pp. 689-706.

Gottesman et al."Bacterial regulation: global regulatory networks," Ann. Rev. Genet., 1984, vol. 18, pp. 415-441.

Greenberg, et al. "Three-year outcomes in deep brain stimulation for highly resistant obsessive-compulsive disorder," Neuropsychopharmacology, 2006, vol. 31, pp. 2384-2393.

Groth et al. "Phage integrases: biology and applications," Journal of Molecular Biology, 2004, vol. 335, pp. 667-678.

Groth, et al. "A phage integrase directs efficient site-specific integration in human cells", PNAS, 2000, vol. 97, No. 11, pp. 5995-6000.

Guatteo, et al. "Temperature sensitivity of dopaminergic neurons of the substantia nigra pars compacta: Involvement of transient receptor potential channels," Journal of Neurophysiol., 2005, vol. 94, pp. 3069-3080.

Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.

Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.

Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.

Hegemann et al., "All-trans Retinal Constitutes the Functional Chromophore in *Chlamydomonas* rhodopsin", Biophys. J., 1991, vol. 60, pp. 1477-1489.

Herry, et al. "Switching on and off fear by distinct neuronal circuits," Nature, 2008, vol. 454, pp. 600-606.

Hirase, et al. "Multiphoton stimulation of neurons", J Neurobiol, 2002, vol. 51, No. 3: pp. 237-247.

Hodaie, et al., "Chronic Anterior Thalamus Stimulation for Intractable Epilepsy," Epilepsia, 2002, vol. 43, pp. 603-608.

Hoffman et al., "K+ Channel Regulation of Signal Propagation in Dendrites of Hippocampal Pyramidal Neurons", 1997, Nature, vol. 387: pp. 869-874.

Hosokawa, T. et al. "Imaging spatio-temporal patterns of long-term potentiation in mouse hippocampus." Philos. Trans. R. Soc. Lond. B., 2003, vol. 358, pp. 689-693.

Hynynen, et al. "Clinical applications of focused ultrasound—The brain." Int. J. Hyperthermia, 2007, vol. 23, No. 2: pp. 193-202.

International Search Report for International Application No. PCT/US2009/053474, dated Oct. 8, 2009.

Johnston et al. "Isolation of the yeast regulatory gene *GAL4* and analysis of its dosage effects on the galactose/melibiose regulon," PNAS, 1982, vol. 79, pp. 6971-6975.

Kandel, E.R.,et al. "Electrophysiology of Hippocampal Neurons: I. Sequential Invasion and Synaptic Organization," J Neurophysiol, 1961, vol. 24, pp. 225-242.

Kandel, E.R.,et al. "Electrophysiology of Hippocampal Neurons: II. After-Potentials and Repetitive Firing", J Neurophysiol., 1961, vol. 24, pp. 243-259.

Karreman et al. "On the use of double FLP recognition targets (FRTs) in the LTR of retroviruses for the construction of high producer cell lines", Nucleic Acids Research, 1996, vol. 24, No. 9: pp. 1616-1624.

Kato et al. "Present and future status of noninvasive selective deep heating using RF in hyperthermia." Med & Biol. Eng. & Comput 31 Supp: S2-11, 1993. Abstract. p. S2 only.

Katz, et al. "Scanning laser photostimulation: a new approach for analyzing brain circuits," Journal of Neuroscience Methods, 1994, vol. 54, pp. 205-218.

Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.

Khossravani et al., "Voltage-Gated Calcium Channels and Idiopathic Generalized Epilepsies", Physiol. Rev., 2006, vol. 86: pp. 941-966.

Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.

Kingston et al. "Transfection of DNA into Eukaryotic Cells," Supplement 63, Current Protocols in Molecular Biology, 1996, 9.1.1-9.1.11, 11 pages.

Kita, H. et al. "Effects of dopamine agonists and antagonists on optical responses evoked in rat frontal cortex slices after stimulation of the subcortical white matter," Exp. Brain Research, 1999, vol. 125, pp. 383-388.

Kitayama, et al. "Regulation of neuronal differentiation by $N$-methyl-D-aspartate receptors expressed in neural progenitor cells isolated from adult mouse hippocampus," Journal of Neurosci Research, 2004, vol. 76, No. 5: pp. 599-612.

Klausberger, et al. "Brain-state- and cell-type-specific firing of hippocampal interneurons in vivo", Nature, 2003, vol. 421: pp. 844-848.

Kocsis et al., "Regenerating Mammalian Nerve Fibres: Changes in Action Potential Waveform and Firing Characteristics Following Blockage of Potassium Conductance", 1982, Proc. R. Soc. Lond., vol. B 217: pp. 77-87.

Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.

Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.

Landy, A. "Mechanistic and structural complexity in the site-specific recombination pathways of Int and FLP", Current Opinion in Genetics and Development, 1993, vol. 3, pp. 699-707.

Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.

Lee et al., "Potassium Channel Gone Therapy Can Prevent Neuron Deatch Resulting from Necrotic and Apoptotic Insults", Journal of Neurochemistry, 2003, vol. 85: pp. 1079-1088.

Lim et al., "A Novel Targeting Signal for Proximal Clustering of the Kv2.1K+ Channel in Hippocampal Neurons", Neuron, 2000, vol. 25: pp. 385-397.

Lima, et al. "Remote Control of Behavior through Genetically Targeted Photostimulation of Neurons", Cell, 2005, vol. 121: pp. 141-152.

Liman, et al. "Subunit Stoichiometry of a Mammalian K+ Channel Determined by Construction of Multimeric cDNAs," Neuron, 1992,vol. 9, pp. 861-871.

Luecke, et al. "Structural Changes in Bacteriorhodopsin During Ion Transport at 2 Angstrom Resolution," Science, 1999, vol. 286, pp. 255-260.

Lyznik, et al. "FLP-mediated recombination of *FRT* sites in the maize genome," Nucleic Acids Research, 1996, vol. 24, No. 19: pp. 3784-3789.

Mann et at. "Perisomatic Feedback Inhibition Underlies Cholinergically Induced Fast Network Oscillations in the Rat Hippocampus in Vitro," Neuron, 2005, vol. 45, 2005, pp. 105-117.

Mattson, "Apoptosis in Neurodegenerative Disorders", Nature Reviews, 2000, vol. 1: pp. 120-129.

Mayberg et al. "Deep Brain Stimulation for Treatment-Resistant Depression," Focus, 2008, vol. VI, No. 1, pp. 143-154.

McKnight "Functional relationships between transcriptional control signals of the thymidine kinase gene of herpes simplex virus", Cell, 1982, vol. 31 pp. 355-365.

Melyan, Z., et al. "Addition of human melanopsin renders mammalian cells Photoresponsive", Nature, 2005, vol. 433: pp. 741-745.

Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.

Meyer, et al. "High density interconnects and flexible hybrid assemblies for active biomedical implants," IEEE Transactions on Advanced Packaging, 2001, vol. 24, No. 3, pp. 366-372.

Monje et al., "Irradiation Induces Neural Precursor-Cell Dysfunction", Natural Medicine, 2002, vol. 8, No. 9, pp. 955-962.

Nacher, et al. "NMDA receptor antagonist treatment increases the production of new neurons in the aged rat hippocampus", Neurobiology of Aging, 2003,vol. 24, No. 2: pp. 273-84.

Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.

Nagel, et al. "Channelrhodopsin-I: a light-gated proton channel in green algae", Science, 2002, vol. 296: pp. 2395-2398.

Nagel, et al. "Channelrhodopsin-2, a directly light-gated cation-selective membrane channel", PNAS, 2003, vol. 100, No. 24: pp. 13940-13945.

Nakagami, et al. "Optical Recording of Trisynaptic Pathway in Rat Hippocampal Slices with a Voltage-Sensitive Dye" Neuroscience, 1997, vol. 81, No. 1, pp. 1-8.

Naqvi, et al. "Damage to the insula disrupts addiction to cigarette smoking," Science; 2007, vol. 315 pp. 531-534.

Nirenberg, et al. "The Light Response of Retinal Ganglion Cells is Truncated by a Displaced Amacrine Circuit", Neuron, 1997, vol. 18: pp. 637-650.

Nunes-Duby, et al. "Similarities and differences among 105 members of the Int family of site-specific recombinases", Nucleic Acids Research, 1998, vol. 26, No. 2: pp. 391-406.

O'Gorman et al. "Recombinase-mediated gene activation and site-specific integration in mammalian cells", Science, 1991, 251(4999): pp. 1351-1355.

Olivares (2001) "Phage R4 integrase mediates site-specific integration in human cells", Gene, 2001, vol. 278, pp. 167-176.

Ory, et al. "A stable human-derived packaging cell line for production of high titer retrovirus/vesicular stomatitis virus G pseudotypes," PNAs, 1996, vol. 93: pp. 11400-11406.

Palmer et al., "The Adult Rat Hippocampus Contains Primordial Neural Stem Cells", Molecular and Cellular Neuroscience, 1997, vol. 8, pp. 389-404.

Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.

"Panda, et al. ""Illumination of the Melanopsin Signaling Pathway""", Science, 2005, vol. 307: pp. 600-604."

Pear "Transient Transfection Methods for Preparation of High-Titer Retroviral Supernatants" Supplement 68, Current Protocols in Molecular Biology, 1996, 9.1 1 .1-9.1 1 .1 8.

Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.

Pettit, et al. "Local Excitatory Circuits in the Intermediate Gray Layer of the Superior Colliculus", J Neurophysiol., 1999, vol. 81, No. 3: pp. 1424-1427.

Potter, "Transfection by Electroporation." Supplement 62, Current Protocols in Molecular Biology, 1996, 9.3.1-9.3.6.

Qiu et al. "Induction of photosensitivity by heterologous expression of melanopsin", Nature, 2005, vol. 433: pp. 745-749.

Rathnasingham et al., "Characterization of implantable microfabricated fluid delivery devices," IEEE Transactions on Biomedical Engineering, 2004, vol. 51, No. 1: pp. 138-145.

Rivera et al., "BDNF-Induced TrkB Activation Down-Regulates the K+-Cl-cotransporter KCC2 and Impairs Neuronal Cl- Extrusion", The Journal of Cell Biology, 2002, vol. 159: pp. 747-752.

Rosenkranz, et al. "The prefrontal cortex regulates lateral amygdala neuronal plasticity and responses to previously conditioned stimuli", J. Neurosci., 2003, vol. 23, No. 35: pp. 11054-11064.

Rousche, et al., "Flexible polyimide-based intracortical electrode arrays with bioactive capability," IEEE Transactions on Biomedical Engineering, 2001, vol. 48, No. 3, pp. 361-371.

Rubinson et at. "A lentivirus-based system to functionally silence genes in primary mammalian cells, stem cells and transgenic mice by RNA interference," Nature Genetics, 2003, vol. 33, p. 401-406.

Rudiger et at. "Specific arginine and threonine residues control anion binding and transport in the light-driven chloride pump halorhodopsin," The EMBO Journal, 1997, vol. 16, No. 13, pp. 3813-3821.

Salzman, et al. "Cortical microstimulation influences perceptual judgements of motion direction", Nature, 1990, vol. 346, pp. 174-177.

Sauer "Site-specific recombination: developments and applications," Current Opinion in Biotechnology, 1994, vol. 5, No. 5: pp. 521-527.

Schiff, et al. "Behavioral improvements with thalamic stimulation after severe traumatic brain injury," Nature, 2007, vol. 448, pp. 600-604.

Schlaepfer et al. "Deep Brain stimulation to Reward Circuitry Alleviates Anhedonia in Refractory Major Depresion," Neuropsychopharmacology, 2008,vol. 33, pp. 368-377.

Sclimenti, et al. "Directed evolution of a recombinase for improved genomic integration at a native human sequence," Nucleic Acids Research, 2001, vol. 29, No. 24: pp. 5044-5051.

Shepherd, et al. "Circuit Analysis of Experience-Dependent Plasticity in the Developing Rat Barrel Cortex", Neuron, 2003, vol. 38: pp. 277-289.

Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.

Silver, et al. "Amino terminus of the yeast *GAL4* gene product is sufficient for nuclear localization" PNAS, 1984, vol. 81, No. 19: pp. 5951-5955.

Singer et al. "Elevated lntrasynaptic Dopamine Release in Tourette's Syndrome Measured by PET," American Journal of Psychiatry, 2002, vol. 159: pp. 1329-1336.

Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.

Smith et al. "Diversity in the serine recombinases", Molecular Microbiology, 2002, vol. 44, No. 2: pp. 299-307.

Stark, et al. "Catalysis by site-specific recombinases," Trends Genet., 1992, vol. 8, No. 12: pp. 432-439.

Stoll, et al. "Phage TP901-I site-specific integrase functions in human cells," Journal of Bacteriology, 2002, vol. 184, No. 13: pp. 3657-3663.

Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.

Tatarkiewicz, et al. "Reversal of Hyperglycemia in Mice After Subcutaneous Transplantation of Macroencapsulated Islets", Transplantation, 1999, vol. 67, No. 5: pp. 665-671.

Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.

Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.

[No Authors Listed] "Two bright new faces in gene therapy," Nature Biotechnology, 1996, vol. 14: p. 556.

Tye et. al., "Amygdala circuitry mediating reversible and bidirectional control of anxiety", Nature, 2011, vol. 471(7338): pp. 358-362.

Tye et. al., Supplementary Materials: "An optically-resolved microcircuit for bidirectional anxiety control", Nature, 2011, vol. 471(7338): pp. 358-362.

Ulmanen, et al. "Transcription and translation of foreign genes in *Bacillus subtilis* by the aid of a secretion vector," Journal of Bacteriology, 1985, vol. 162, No. 1: pp. 176-182.

Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.

Vanin, et al. "Development of high-titer retroviral producer cell lines by using Cre-mediated recombination," Journal of Virology, 1997, vol. 71, No. 10: pp. 7820-7826.

Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.

Wagner, "Noninvasive Human Brain Stimulation", Annual Rev. Biomed. Eng. 2007. 9:19.1-19.39.

Ward, et al. "Construction and characterisation of a series of multicopy promoter-probe plasmid vectors for *Streptomyces* using the aminoglycoside phosphotransferase gene from Tn5 as indicator", 1986, Mol. Gen. Genet., vol. 203: pp. 468-478.

Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.

Wang et al. "Direct-current Nanogenerator Driven by Ultrasonic Waves," Science, 2007, vol. 316, pp. 102-105.

Wang et. al., "High-speed mapping of synaptic connectivity using photostimulation in Channelrhodopsin-2 transgenic mice", PNAS, 2007, vol. 104, No. 19, pp. 8143-8148.

Witten et. al., Supporting Online Material for: "Cholinergic Interneurons Control Local Circuit Activity and Cocaine Conditioning", Science, 2010, vol. 330: 17 pages.

Witten et. al., "Cholinergic Interneurons Control Local Circuit Activity and Cocaine Conditioning", Science, 2010, vol. 330, No. 6011: pp. 1677-1681.

Yamazoe, et al. "Efficient generation of dopaminergic neurons from mouse embryonic stem cells enclosed in hollow fibers", Biomaterials, 2006, vol. 27, pp. 4871-4880.

Yizhar et. al., "Neocortical excitation/inhibition balance in information processing and social dysfunction", Nature, 2011, vol. 477, pp. 171-178; and Supplemental Materials; 41 pages.

Yoon, et al., "A micromachined silicon depth probe for multichannel neural recording," IEEE Transactions Biomedical Engineering, 2000, vol. 47, No. 8, pp. 1082-1087.

Yoshimura, et al. "Excitatory cortical neurons form fine-scale functional networks", Nature, 2005, vol. 433: pp. 868-873.

Zacharias et al. "Recent advances in technology for measuring and manipulating cell signals," Current Opinion in Neurobiology, 2000, vol. 10: pp. 416-421.

Zemelman, et al. "Selective Photostimulation of Genetically ChARGed Neurons", Neuron, 2002, vol. 33: pp. 15-22.

Zemelman, et al. "Photochemical gating of heterologous ion channels: Remote control over genetically designated populations of neurons", PNAS, 2003, vol. 100, No. 3: pp. 1352-1357.

Zhang, et al. "Channelrhodopsin-2 and optical control of excitable cells," Nature Methods,2006, vol. 3, No. 10, pp. 785-792.

Zhang, et al. "Red-Shifted Optogenetic Excitation: a Tool for Fast Neural Control Derived from *Volvox carteri*", Nature Neurosciences, 2008,vol. 11, No. 6, pp. 631-633.

Zrenner, E., "Will Retinal Implants Restore Vision?" Science, 2002, vol. 295, No. 5557, pp. 1022-1025.

Zufferey, et al. "Self-Inactivating Lentivirus Vector for Safe and Efficient In Vivo Gene Delivery", Journal of Virology, 1998, vol. 72, No. 12, pp. 9873-9880.

K. Isenberg et al., "*Cloning of a Putative Neuronal Nicotinic Aceylcholine Receptor Subunit*," Journal of Neurochemistry, New York, pp. 988-991 (1989).

E. Bamberg et al., "*Light-driven proton or chloride pumping by halorhodopsin*," Proc. Natl. Academy Science USA, vol. 90, No. 2, pp. 639-643 (Jan. 1993).

Hildebrandt et al., "*Bacteriorhodopsin expressed in Schizosacch263aromyces pombe pumps protons through the plasma membrane*," PNAS 90, pp. 3578-3582 (Apr. 1993).

E. Levitan et al., "*Surface Expression of kvl Voltage-Gated $K^+$ Channels Is Governed by a C-terminal Motif*," TCM, vol. 10, No. 7, pp. 317-320 (2000).

K. Petrecca et al., "*Localization and Enhanced Current Density of the kv4.2 Potassium Channel by Interaction with the Actin-Binding Protein Filamin*," The Journal of Neuroscience, vol. 20, No. 23, pp. 8736-8744 (Dec. 1, 2000).

G. Ensell et al., "Silicon-based microelectrodes for neurophysiology, micromachined from silicon-on-insulator wafers," Med. Biol. Eng. Comput. 38:175-179 (2000).

D. Ma et al., "*Role of ER Export Signals in Controlling Surface Potassium Channel Numbers*," Science, vol. 291, pp. 316-319 (Jan. 12, 2001).

C. Stockklausner et al., "*A sequence motif responsible for ER export and surface expression of Kir2.0 inward rectifier $K^+$ channels*," FEBS letters, vol. 493, pp. 129-133 (2001).

J. Weick et al., "*Interactions with PDZ Proteins Are Required for L-Type Calcium Channels to Activate cAMP Response Element-Binding Protein-Dependent Gene Expression*," The Journal of Neuroscience, vol. 23, No. 8, pp. 3446-3456 (Apr. 15, 2003).

F. Pauhle et al., "*Specific Endoplasmic Reticulum Export Signal Drives Transport of Stem Cell Factor (Kitl) to the Cell Surface*," The Journal of Biological Chemistry, vol. 279, No. 53, pp. 55545-55555 (Dec. 31, 2004).

Z.-H. Pan et al., "*Functional Expression of a Directly Light-Gated Membrane Channel in Mammalian Retinal Neurons: A Potential Strategy for Restoring Light Sensitivity to the Retina After Photoreceptor Regeneration*," Investigative Opthalmology & Visual Science 46 E-Abstract 4631 (May 1, 2005). Abstract only.

Sato et al., "*Role of Anion-binding Sites in cytoplasmic and extracellular channels of Natronomonas pharoaonis halorhodopsin*," Biochemistry, 44, 4775-4784 (2005).

E. S. Boyden of al., "*Millisecond-timescale, genetically targeted optical control of neural activity*," Nature Neuroscience 8(9): 1263-1268; and the abstract (Aug./Sep. 2005).

X. Li et al., "*Fast noninvasive activation and inhibition of neural and network activity by vertebrate rhodopsin and green algae channelrhodopsin*," PNAS, vol. 102, No. 49, pp. 17816-17821 (online Nov. 23, 2005).

N. Bocquet et al., "*A prokaryotic proton-gated ion channel from the nicotinic acetylcholine receptor family*," Nature Letters, vol. 445, pp. 116-119 (Jan. 2007).

Zhang et al., "*Multimodal fast optical interrogation of neural circuitry*," Nature, 446, pp. 633-635 (2007).

L. Campagnola et al., "*Fiber-coupled light-emitting diode for localized photostimulation of neurons expressing channelrhodopsin-2*," Journal of Neuroscience Methods 169(1): 27-33 (Mar. 2008). Abstract only.

Cell Biology: Optical excitation yin and yang www.signaling-gateway.org/update/updates/20075/nmeth0507-384.html.

De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.

Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.

Gold, et al. "Representation of a perceptual decision in developing oculomotor commands", Nature, 2000, vol. 404, pp. 390-394.

Gregory, et al. "Integration site for Streptomyces phage φBT1 and development of site-specific integrating vectors", Journal of Bacteriology, 2003, vol. 185, No. 17, pp. 5320-5323.

Gulick, et al. "Transfection using DEAE-Dextran" Supplement 40, Current Protocols in Molecular Biology, 1997, Supplement 40, 9.2.1-9.2.10.

Airan, et al. "Temporally Precise in vivo Control of Intracellular Signaling", 2009, Nature, vol. 458, No. 7241, pp. 1025-1029.

Braun, "Two Light-activated Conductances in the Eye of the Green Alga *Volvox carteri*", 1999, Biophys J., vol. 76, No. 3, pp. 1668-1678.

Cardin, et al. "Driving Fast spiking Cells Induces Gamma Rhythm and Controls Sensory Responses", 2009, Nature, vol. 459, vol. 7247, pp. 663-667.

Deisseroth et al., "Excitation-neurogenesis Coupling in Adult Neural Stem/Progenitor Cells", 2004, Neuron, vol. 42, pp. 535-552.

Ernst, et al. "Photoactivation of Channelrhodopsin", 2008, vol. 283, No. 3, pp. 1637-1643.

Genbank Accession No. DQ094781 (Jan. 15, 2008).

Gradinaru, et al. "ENpHR: a Natronomonas Halorhodopsin Enhanced for Optogenetic Applications", 2008, Brain Cell Biol., vol. 36 (1-4), pp. 129-139.

Herlitze, et al., "New Optical Tools for Controlling Neuronal Activity", 2007, Curr Opin Neurobiol, vol. 17, No. 1, pp. 87-94.

Jekely, "Evolution of Phototaxis", 2009, Phil. Trans. R. Soc. B, vol. 364, pp. 2795-2808.

Johansen, et al., "Optical Activation of Lateral Amygdala Pyramidal Cells Instructs Associative Fear Learning", 2010, PNAS, vol. 107, No. 28, pp. 12692-12697.

Kianianmomeni, et al. "Channelrhodopsins of *Volvox carteri* are Photochromic Proteins that are Specifically Expressed in Somatic Cells under Control of Light, Temperature, and the Sex Inducer", 2009, Plant Physiology, vol. 151, No. 1, pp. 347-366.

Knopfel, et al. "Optical Probin of Neuronal Circuit Dynamics: Gentically Encoded Versus Classical Fluorescent Sensors", 2006, Trends Neurosci, vol. 29, No. 3, pp. 160-166.

McAllister, "Cellular and Molecular Mechanisms of Dendrite Growth", 2000, Cereb Cortex, vol. 10, No. 10, pp. 963-973.

Pape, et al., "Plastic Synaptic Networks of the Amygdala for the Acquisition, Expression, and Extinction of Conditioned Fear", 2010, Physiol Rev, vol. 90, pp. 419-463.

Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.

Randic, et al. "Long-term Potentiation and Long-term Depression of Primary Afferent Neurotransmission in the Rat Spinal Cord", 1993, Journal of Neuroscience, vol. 13, No. 12, pp. 5228-5241.

Ritter, et al., "Monitoring Light-induced Structural Changes of Channelrhodopsin-2 by UV-Visable and Fourier Transform Infared Spectroscopy", 2008, The Journal of Biological Chemistry, vol. 283, No. 50, pp. 35033-35041.

Sajdyk, et al., "Excitatory Amino Acid Receptors in the Basolateral Amygdala Regulate Anxiety Responses in the Social Interaction Test", Brain Research, 1997, vol. 764, pp. 262-264.

Swanson, "Lights, Opsins, Action! Optogenetics Brings Complex Neuronal Circuits into Sharper Focus", 2009, the Dana Foundation, [URL: http://www.dana.org/news/features/detail.aspx?id=24236], PDF File, pp. 1-3.

Swiss-Prot_Q2QCJ4, Opsin 1, Oct. 31, 2006, URL: http://www.ncbi.nlm.nig.gov/protein/Q2QCJ4.

"SubName: Full=Channelrhodopsin-1", retrieved from EBI accession No. UNIPROT: B4Y103. Database accession No. B4Y103. Sep. 23, 2008.

Hausser, et al. "Tonic Synaptic Inhibition Modulates Neuronal Output Pattern and Spatiotemporal Synaptic Integration", Neuron, 1997, vol. 19, pp. 665-678.

Kingston et al. "Transfection and Expression of Cloned DNA," Supplement 31, Current Protocols in Immunology, 1999, 10.13.1-1 0.13.9.

Louis et al. "Cloning and sequencing of the cellular-viral junctions from the human adenovirus type 5 transformed 293 cell line," Virology, 1997, vol. 233, pp. 423-429.

Mortensen et al. "Selection of Transfected Mammalian Cells," Supplement 86, Current Protocols in Molecular Biology, 1997, 9.5.1-09.5.19.

Pear "Transient Transfection Methods for Preparation of High-Titer Retroviral Supernatants" Supplement 68, Current Protocols in Molecular Biology, 1996, 9.1 1 .I-9.1 1 .I8.

Pouille, et al. "Routing of spike series by dynamic circuits in the hippocampus", Nature, 2004, vol. 429: pp. 717-723.

Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.

Song, "Genes responsible for native depolarization-activated K+ currents in neurons," Neuroscience Research, 2002, vol. 42, pp. 7-14.

Wells et al. "Application of Infrared light for in vivo neural stimulation," Journal of Biomedical Optics, 2005, vol. 10(6), pp. 064003-1-064003-12.

Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.

Han, et al., "Multiple-Color Optical Activiation, Silencing, and Desynchronization of Neural Activity, with Single-Spike Temporal Resolution", PLos One, 2007, Isses 3, 12 pages.

Zhang, et al., "Multimodal Fast Optical Interrogation of Neural Circuitry", Nature, 2007, vol. 446, pp. 633-641.

U.S. Appl. No. 13/299,727, filed Nov. 18, 2011, Lee, et al.

\* cited by examiner

SYSTEM FOR OPTICAL STIMULATION OF TARGET CELLS

RELATED PATENT DOCUMENTS

This patent document is the national stage filing under 35 U.S.C. §371 of International Application No. PCT/US2008/050745 filed on Jan. 10, 2008, which claims benefit under 35 U.S.C. §119(e) both of U.S. Provisional Application No. 60/879,669 filed on Jan. 10, 2007 and entitled "Genetically-Targetable Optical Inactivation of Excitable Cells" and of U.S. Provisional Application No. 60/903,248 filed on Feb. 23, 2007 and entitled "Genetically-Targetable Optical Inactivation of Excitable Cells," each of which are fully incorporated by reference.

INCORPORATION-BY-REFERENCE OF MATERIAL SUBMITTED ELECTRONICALLY

Incorporated by reference in its entirety is a computer-readable nucleotide/amino acid sequence listing submitted concurrently herewith, and identified as follows: One 2,460 Byte ASCII (Text) file named "PCTUS2008050745.txt" created on Mar. 27, 2008.

FIELD OF THE INVENTION

The present invention relates generally to systems and approaches for stimulating target cells, and more particularly, to using optics to dissuade stimulation-generated pulse trains.

BACKGROUND

Various efforts in neuroscience are directed towards determining whether neural activity in a specific brain region, or in a set of genetically-identified neurons, contributes to a particular neural computation, behavior, or neurological or psychiatric disorder. For centuries, insights have come from studies of human patients with specific lesions, as exemplified by Paul Broca's delineation in the 1860s of the eponymous brain area that, when dysfunctional, results in deficits of speech production. Many studies have used ablation or pharmacological shutdown of neurons or brain regions in animals, or careful analysis of patients, to parse out the physical substrates of normal and abnormal behavior. However, growing awareness that activity in multiple brain regions may be coordinated during performance of a behavior, or in a particular neural dysfunction, has raised the question of precisely when specific brain regions or neurons contribute. For example, a large number of in vivo recording studies have demonstrated, for many brain regions, that specific neurons can fire action potentials during precise intervals within a behavioral task. The intervals can last as little as a fraction of a second; it is possible that specific brain regions or neurons are required only at specific times in a task, not continuously. In humans, use of transcranial magnetic stimulation to disrupt the visual cortex has demonstrated that conscious perception requires intact cortical performance during temporal windows that last tens of milliseconds, occurring at precise times after visual stimulus presentation. Accordingly, a method for disrupting activity in targeted cell types for very precisely delimited periods of time (e.g., several milliseconds) could help answer a number of outstanding questions, and enable novel ones to be asked. For example, one question involves the identification of the precise brain regions, cell types, and activity patterns required at each phase (sensory, decision-making and motor) of a behavioral task. Another question involves, for a particular perception (e.g., feeling, decision, memory, or action) identifying the precise number of neurons that must be active within a certain region and how long the neurons are active. Another question involves the identification of the causal role of neural synchrony and precise spike timing in neural computation, plasticity, and pathological brain function. As memories are encoded, consolidated, and forgotten, it can be important to identifying how the critical neural loci of memory changes.

SUMMARY

The claimed invention is directed to photosensitive biomolecular structures and related methods. The present invention is exemplified in a number of implementations and applications, some of which are summarized below.

According to one example embodiment of the present invention, a method is implemented for optical stimulation of a cell expressing an NpHR ion pump. The method includes the step of providing a sequence of stimuli to the cell. Each stimulus increases the probability of depolarization events occurring in the cell. Light is provided to the cell to activate the expressed NpHR ion pump, thereby decreasing the probability of depolarization events occurring in the cell.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

Figure 1:
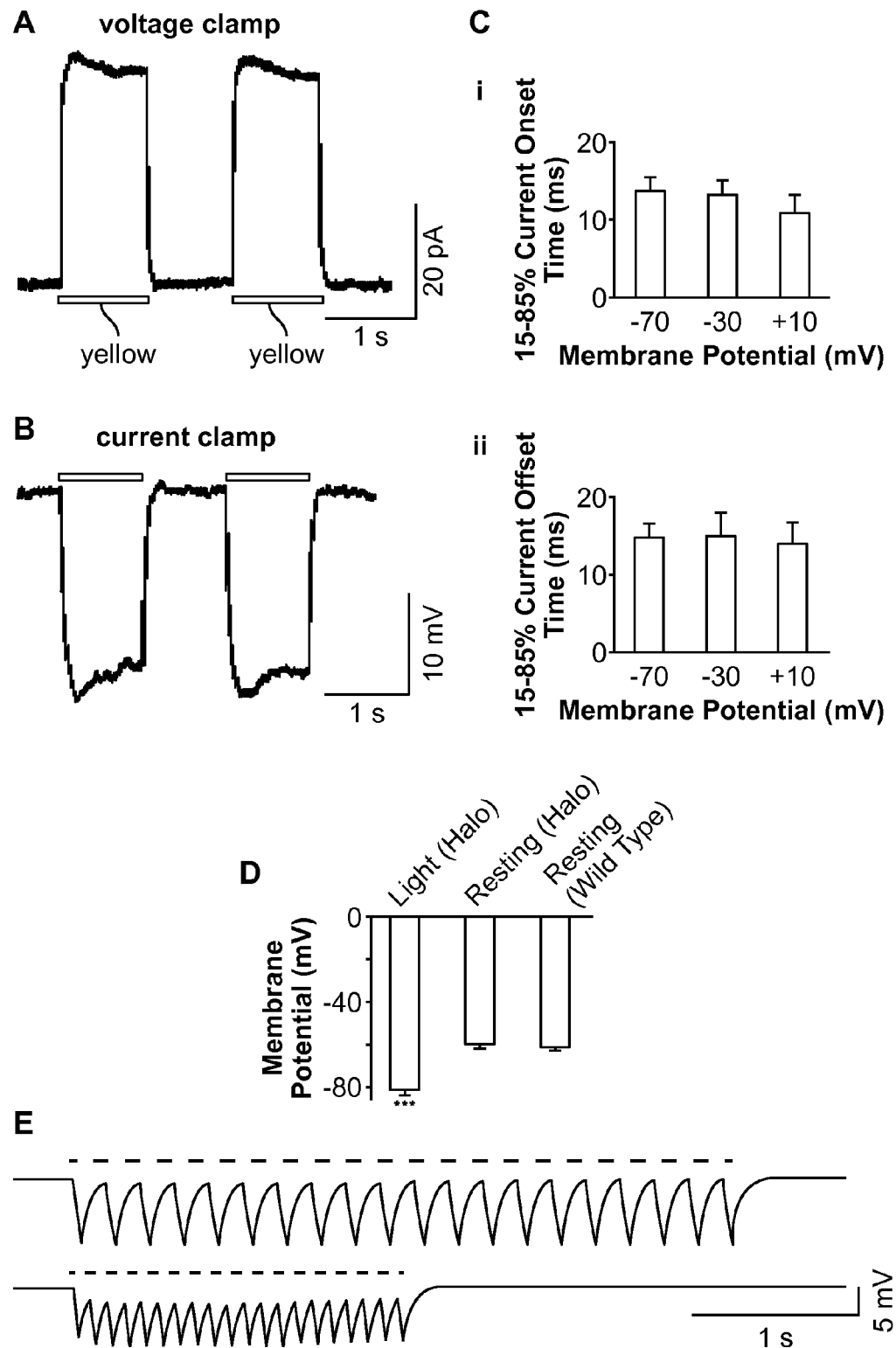
FIG. 1A shows sample outward currents elicited by two pulses of yellow light in a voltage-clamped neuron, consistent with an embodiment of the present invention.
FIG. 1B shows sample membrane voltage hyperpolarizations elicited by two pulses of yellow light, in a current-clamped neuron held at resting membrane potential, consistent with an embodiment of the present invention.
FIG. 1C shows Kinetic properties of yellow light-elicited, Halo-mediated currents from voltage-clamped neurons, consistent with an embodiment of the present invention.
FIG. 1D shows membrane potentials of neurons expressing Halo-GFP and exposed to yellow light, neurons expressing Halo-GFP but not exposed to any light, and neurons without transfection with Halo-GFP, consistent with an embodiment of the present invention.
FIG. 1E shows sample membrane hyperpolarizations induced by 5 Hz and 10 Hz trains of yellow light pulses, consistent with an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for enabling practical application of a variety of photosensitive bio-molecular structures, and the invention has been found to be particularly suited for use in arrangements and methods dealing with neuron stimulation. While the present invention is not necessarily limited to such applications, various aspects of the invention may be appreciated through a discussion of various examples using this context.

The aspects of the present invention are directed to a technology that enables rapid neural inactivation and release from inactivation at the millisecond timescale, is safe and effective, has minimal effects on cellular physiology or survival, and requires no exogenous chemicals to be delivered. A specific embodiment of the invention involves a single-component protein capable of mediating light-induced inhibition, the mammalian codon-optimized version of the light-driven chloride pump halorhodopsin, from the archaebacterium *Natronobacterium pharaonis* (abbreviated Halo). Although such halobacteria are known to live in very high saline concentrations (e.g., >1 M), some wild-type halorhodopsins have been shown to preserve functionality at much lower chloride concentrations, even at levels comparable to those found in mammalian cerebrospinal fluid. Applications of the present invention involve the use of Halo to mediate optical inhibition of neuronal spiking in a physiologically accurate milieu, in response to pulses of somatically injected intracellular current (~300 PA), with temporal onset and offset of inhibition in the range of 10-15 milliseconds. Moreover, Halo can mediate naturalistic trains of inhibitory voltage changes at physiologically relevant frequencies, with minimal attenuation of voltage amplitude from pulse to pulse.

Aspects of an embodiment of the invention are also directed to a single neuron expressing both Halo and the blue-light driven cation channel Channelrhodopsin-2 (ChR2), neural inhibition and excitation are controlled at the millisecond timescale by pulses of yellow and blue light, respectively. In one instance, these channels provide the capability to create lesions of virally or transgenically targeted neural circuits over precise timescales, as well as neuroengineering interfaces for bi-directional control of excitable cell depolarization and hyperpolarization.

One embodiment of the present invention involves a designed fusion protein having the mammalian codon-optimized form of *N. pharaonis* halorhodopsin (Halo), with EGFP added in-frame at the C-terminus for ease of visualization. When expressed using the CaMKII promoter, which targets excitatory neurons of the forebrain, Halo-EGFP fluoresced brightly and appeared evenly distributed in the neuron. When exposed to ~10 mW/mm$^2$ yellow light (e.g., from a xenon lamp, filtered by a standard Texas red excitation filter (bandpass, 560±27.5 nm, Chroma), voltage-clamped hippocampal neurons expressing Halo can experience outward currents with rapid onset, stable steady-state, and abrupt shut-off with cessation of illumination. In some instances, no supplementation of the culture medium or the recording medium with the halorhodopsin cofactor all-trans retinal is necessary. This is believed to be due to levels of all-trans retinal naturally occurring in mammalian neurons in culture and in live brain that are high enough to enable type I opsins without chemical supplementation.

FIG. 1 shows the results of an experimental test of millisecond-timescale, yellow light-driven, neuronal hyperpolarization with Halo. A cultured hippocampal neuron expressing mammalian codon-optimized *N. pharaonis* halorhodopsin (Halo) fused to GFP under the CaMKII promoter is used.

FIG. 1A shows sample outward currents elicited by two 1-second pulses of yellow (560±27.5 nm) light (~10 mW/mm$^2$) in a voltage-clamped neuron held at −70 mV. Yellow bars in this and subsequent figures indicate the period of yellow light exposure.

FIG. 1C shows Kinetic properties of yellow light-elicited, Halo-mediated currents from voltage-clamped neurons. FIG. 1Ci shows 15-85% current onset time. FIG. 1Cii shows 85-15% offset time. For each measurement, data is presented from neurons held at −70 mV (n=14 neurons), −30 mV (n=10), and +10 mV (n=10) (left to right). Bars represent mean±standard error of the mean (S.E.M.).

FIG. 1B shows sample membrane voltage hyperpolarizations elicited by two 1-second pulses of yellow light, in a current-clamped neuron held at resting membrane potential.

FIG. 1D shows membrane potentials of neurons expressing Halo-GFP and exposed to yellow light (left, n=14), expressing Halo-GFP but not exposed to any light (middle, n=11), and without transfection with Halo-GFP (right, n=8). *** denotes significant difference between the Halo-GFP+light condition and each of the other two conditions (p<0.0001; Fisher's partial least-squares difference (PLSD) post hoc test after ANOVA).

FIG. 1E shows sample membrane hyperpolarizations induced by 5 Hz (top) and 10 Hz (bottom) trains of yellow light pulses, with light pulse durations of 50 ms (top) and 25 ms (bottom), respectively.

In related experimental tests, the light pulses elicited pulse amplitudes of 56.9±23.4 pA (mean±st. dev.; n=14 neurons). Repeating a 1-second pulse of yellow light twice, spaced by 1 second in darkness, resulted in identical pulse amplitudes each time (p>0.50, paired t-test), as shown in FIG. 1A.

This stable current amplitude appears to be consistent with what is known about the halorhodopsin photocycle. As befits a chloride pump, the current amplitude did not vary significantly with holding voltage (F=0.004, p>0.95, ANOVA with factor of holding voltage), nor did any measured kinetic parameters vary, such as the onset or offset times of the current pulses (F<0.6, p>0.55 for all comparisons, ANOVA; FIG. 1C). The onset and offset times of elicited currents were seen to be on the order ~10-15 ms at all holding voltages tested. This suggests that Halo is a viable candidate for ultratransient shutdown of spike trains (FIG. 1Ci, 1Cii). When held in current clamp, hippocampal neurons underwent peak hyperpolarizations of −21.6±11.3 mV (mean±st. dev.; n=11 neurons) in response to pulses of yellow light, with no difference between the peak hyperpolarizations achieved by two pulses separated by a 1-second pause (p>0.85, paired t-test; FIG. 1B). These large voltage changes were relatively rapid, with onset and offset times of 68±57 and 73±39 ms, respectively. Thus, Halo has been shown to be capable of reliably mediating hyperpolarizations of significant magnitude, with fast onset and offset times at the beginning and end of light exposure.

Several control experiments were implemented to evaluate whether Halo has unanticipated side effects, such as altering basal cell physiology or increasing the propensity for cell death. First, the basal state of Halo-expressing neurons electrophysiologically was characterized when no light was present. When measured in darkness, no difference was seen between the resting potentials of neurons expressing Halo and those of neighboring neurons in the culture that were untransfected (p>0.20, n=11 Halo-positive cells, n=8 Halo-negative cells; FIG. 1D). This result suggests that basal neural activity would be little affected by the presence of Halo. On the other hand, Halo-expressing neurons illuminated with yellow light were significantly hyperpolarized, with respect to both Halo-expressing neurons in darkness and non-transfected cells (p<0.0001 for both of these comparisons, Fisher's partial least squares difference post hoc test after ANOVA (F=28.4, p<0.0001) with factor of experimental condition; FIG. 1D). An independent assay for unanticipated effects on cell health, the membrane-impermeant DNA stain ethidium homodimer-1 was used to detect the cell membrane breakdown accompanying cell death for one week in Halo-expressing cells. Little difference was found in the prevalence of cell death between Halo-positive and Halo-negative neurons: 16/308 (5.2%) non-transfected neurons counted, and 1/22 (4.5%) Halo-expressing neurons counted, were labeled by ethidium homodimer-1, indicating that Halo was not toxic over the course of the one-week experiment ($x2=0.02$, p>0.85).

In an effort to explore the uses Halo could present in the analysis and engineering of intact neural circuits, an experiment was performed to determine whether the fast response times of Halo could support naturalistic sequences of hyperpolarization events, in response to trains of brief pulses of yellow light.

Figure 2:
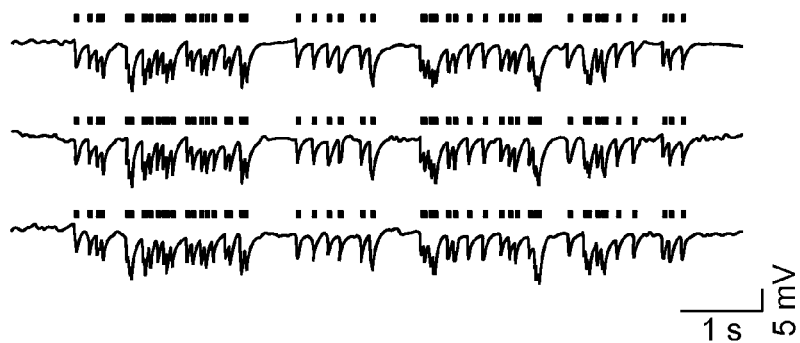
FIG. 2A shows three voltage traces of a current-clamped hippocampal neuron, exposed to a Poisson train of yellow light pulses, consistent with an embodiment of the present invention.
FIG. 2B shows voltage traces of three different current-clamped neurons exposed to the same Poisson train of light pulses ($\lambda$=100 ms), consistent with an embodiment of the present invention.
FIG. 2C shows properties of hyperpolarization events elicited by Poisson trains with various inter-pulse intervals, consistent with an embodiment of the present invention.
FIG. 2D shows a comparison of the peak hyperpolarization and the time-to-peak data at the beginning and end of the Poisson trains, for the neurons described in FIG. 2C, consistent with an embodiment of the present invention.
Figure 2:
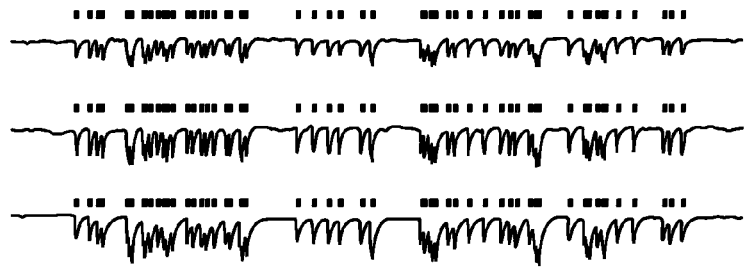
Figure 2:
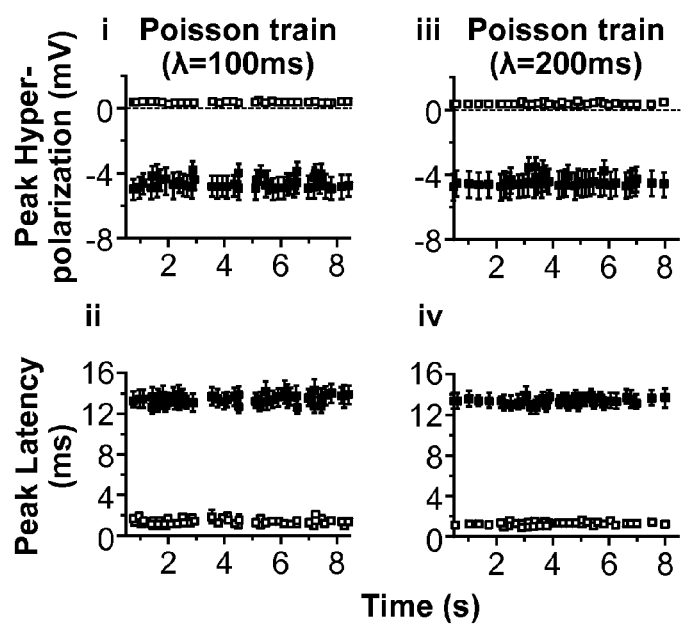
Figure 2:
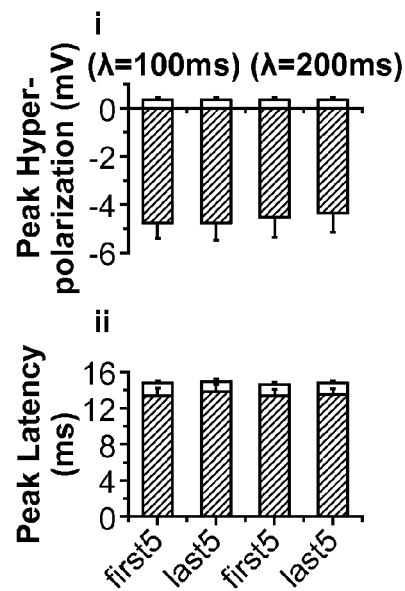

FIG. 2 shows high-fidelity Halo-mediated naturalistic trains of inhibitory events. FIG. 2A shows three voltage traces of a current-clamped hippocampal neuron, exposed to a Poisson train of yellow light pulses. Each light pulse lasts 10 ms, and the Poisson train has a mean inter-pulse interval of $\lambda=100$ ms.

FIG. 2B shows voltage traces of three different current-clamped neurons exposed to the same Poisson train of light pulses ($\lambda=100$ ms).

FIG. 2C shows properties of hyperpolarization events elicited by Poisson trains with inter-pulse interval $\lambda=100$ ms (i, ii) and $\lambda=200$ ms (iii, iv), plotted versus onset time of each light pulse. Plots (i) and (iii) show the peak of each hyperpolarization event, as well as the across-trials standard deviation of these amplitude values across ten trials. Plots (ii) and (iv) show the latency between the onset time of the light pulse and the time of the hyperpolarization peak, as well as the across-trials standard deviation of these timing values across ten trials. All plotted points are across-neuron mean±S.E.M. (n=5 neurons).

FIG. 2D shows a comparison of the peak hyperpolarization (i) and the time-to-peak (ii) data at the beginning (first 5) and end (last 5) of the $\lambda=100$ ms and $\lambda=200$ ms Poisson trains, for the n=5 neurons described in FIG. 2C. In (i): for each neuron, the average of the first 5 or last 5 hyperpolarization peaks or the across-trials standard deviation of these amplitude values was first computed, then the across-neuron mean±S.E.M. was plotted. In (ii): for each neuron, the average of the first 5 or last 5 times-to-peak or the across-trials standard deviation of these times-to-peak were first computed, then the across-neuron mean±S.E.M. was plotted.

FIG. 2A shows three traces of hyperpolarization events elicited in a single neuron, resulting from repeatedly playing back a Poisson train (mean inter-pulse interval, $\lambda=100$ ms, 59 pulses), of 10 ms-duration yellow light pulses, to simulate stochastic synaptic inhibitory input. FIG. 2B shows three such hyperpolarization traces, taken from different neurons. The variability of such trains was remarkably low in many regards—across ten repeated trials in a single cell, across multiple cells (n=5 neurons), and over time throughout a sustained train of 59 pulses (FIG. 2C, 2D). It was found that for hyperpolarizations elicited by 10 ms-duration light pulses during a $\lambda=100$ ms Poisson train, the mean amplitude was −4.56 mV (averaged across trials and neurons), but the trial-to-trial standard deviation of this amplitude was only 0.40 mV (averaged across neurons, FIG. 2Ci and FIG. 2Di). The trial-to-trial jitter of the time the hyperpolarization took to reach its peak value was also small, 1.27 ms (averaged across neurons, FIG. 2Cii and FIG. 2Dii). The neuron-to-neuron variability of amplitude and timing was somewhat larger than the trial-to-trial variability, with standard deviations of 1.45 mV and 1.78 ms, respectively, but demonstrating that precise inhibitory control of a population of neurons could proceed with millivolt and millisecond resolution. Finally, the through-train sustainability of light-elicited voltage changes was quantitatively examined by comparing the amplitude mean and amplitude variability, and timing variability of the hyperpolarization events elicited by the first five light pulses to those of the last five light pulses in the train (FIGS. 2Di and 2Dii, left side). Little or no difference was seen for any of these statistics between the beginning and end of a train (p>0.10 for all measures, t-test). Identical conclusions held for the $\lambda=200$ ms Poisson train with 46 pulses (FIGS. 2Ciii and 2Civ, and FIGS. 2Di and 2Dii, right side). The high temporal and amplitude fidelity of Halo-mediated hyperpolarizations suggests uses for Halo in simulating inhibitory synaptic inputs, with great precision.

Figure 3:
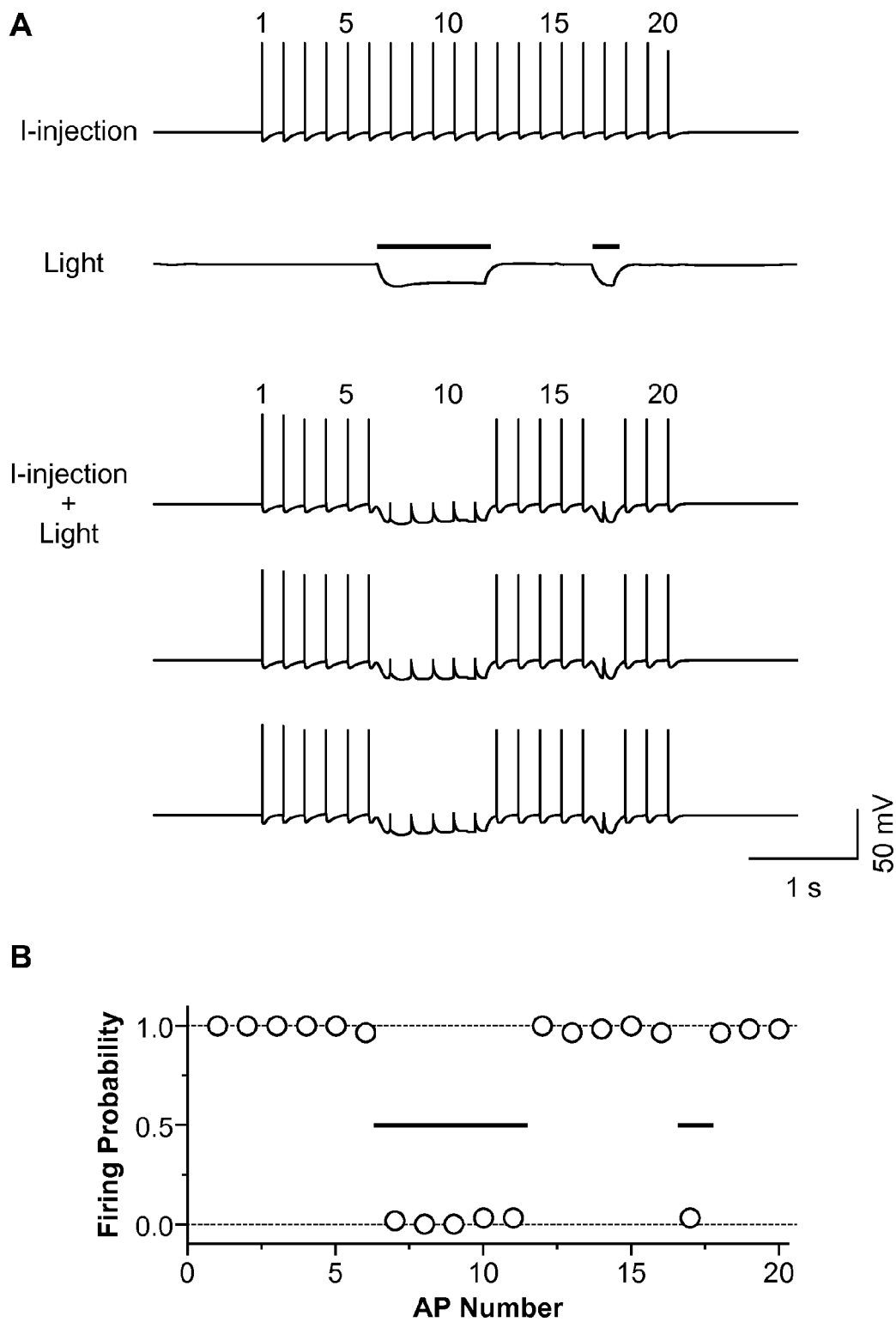
FIG. 3A shows a light-driven spike blockade, demonstrated for a single hippocampal neuron, consistent with an embodiment of the present invention.
FIG. 3B shows population data (n=6 neurons) for light-driven, Halo-mediated spike blockade, consistent with an embodiment of the present invention.

FIG. 3 shows reliable and repeatable Halo-mediated neural inactivation, at single-spike temporal resolution. FIG. 3A shows a light-driven spike blockade, demonstrated for a single hippocampal neuron. At the top of FIG. 3A, labeled with "I-injection," neuronal firing of 20 spikes at 5 Hz are induced by pulsed somatic current injection (~300 pA, 4 ms). In the middle of FIG. 3A, labeled with "light," light membrane hyperpolarizations are induced by two periods of yellow light, timed so as to be capable of blocking spikes 7-11 and spike 17 out of the train of 20 spikes. At the bottom of FIG. 3A, labeled as "I-injection+Light", yellow light drives Halo to block neuron spiking (note significant reductions of spikes 7-11 and of spike 17), while leaving spikes elicited during periods of darkness largely intact.

FIG. 3B shows population data (n=6 neurons) for light-driven, Halo-mediated spike blockade, showing high spike probability during periods of darkness (spikes 1-6, 12-16, and 18-20), and low spike probability during periods of yellow-light illumination (spikes 7-11 and spike 17). Error bars are smaller than the points plotted.

Such experiment were implemented to analyze the ability of Halo to enable rapidly inducible and reversible silencing of neuron spiking. Such ability can be useful to enable time-resolved parsing of the precise neural substrates of behavior. Neurons were intracellularly injected with trains of somatic current pulses (~300 PA, lasting ~4 ms), causing them to fire action potentials at 5 Hz with 100% success rate (FIG. 3A, "I-injection"). Yellow-light pulses were scheduled to occur during the times when certain spikes (i.e., spikes 7-11 and 17) would occur during the somatic current injection protocol (FIG. 3A). The light pulses and the somatic current pulses were presented together (FIG. 3A, "I-injection+light", three trials shown). Spiking was effectively blocked during the periods of yellow-light exposure. The rapid onset and offset kinetics of Halo allowed the deletion of even single spikes. For instance, the second yellow-light pulse, timed for silencing just spike 17, was able to effectively eliminate spike 17 without affecting the firing of spikes 16 or 18 at all. The experiment was repeated five times on each of n=6 neurons (FIG. 3B). During periods when the yellow light was off, it was found that somatic current pulses elicited a spike 98.7% of the time. In contrast, during periods when the yellow light was on, somatic current pulses elicited a spike only 1.2% of the time. The second pulse of yellow light reduced the probability of firing spike 17 to 3.3%, whereas spikes 16 and 18 still fired 96.7% of the time, not significantly different from the spikes at the beginning of the train, before any light exposure at all ($X^2=1.02$, $p>0.30$). The temporal precision of Halo in silencing spikes therefore offers the possibility of creating ultratransient (yet precise and effective) lesions of activity in targeted neurons.

A specific embodiment of the present invention includes the use of one member of the type I opsin family, Channelrhodopsin-2 (ChR2), which has received recent attention for its ability to drive neural excitation in response to pulses of blue light (centered around 470 nm). The ability to drive excitation and inhibition in the same neuron, using two different wavelengths of light, could enable answers to questions for which no current technology peinlits resolution. For example, synchronous neural activity has been correlated with higher-order functions, such as attention and abnormal patterns of neural synchrony that are associated with certain neurological and psychiatric disorders. The ability to drive a neuron with balanced but randomly varying excitation and inhibition may allow alteration of the precise timing of membrane voltage fluctuations, in principle permitting neural synchronization or desynchronization without any side effects, such as alteration of spike rate. This may open up new experiments in testing the causal role of neural synchrony in behavior and pathology.

Figure 4:
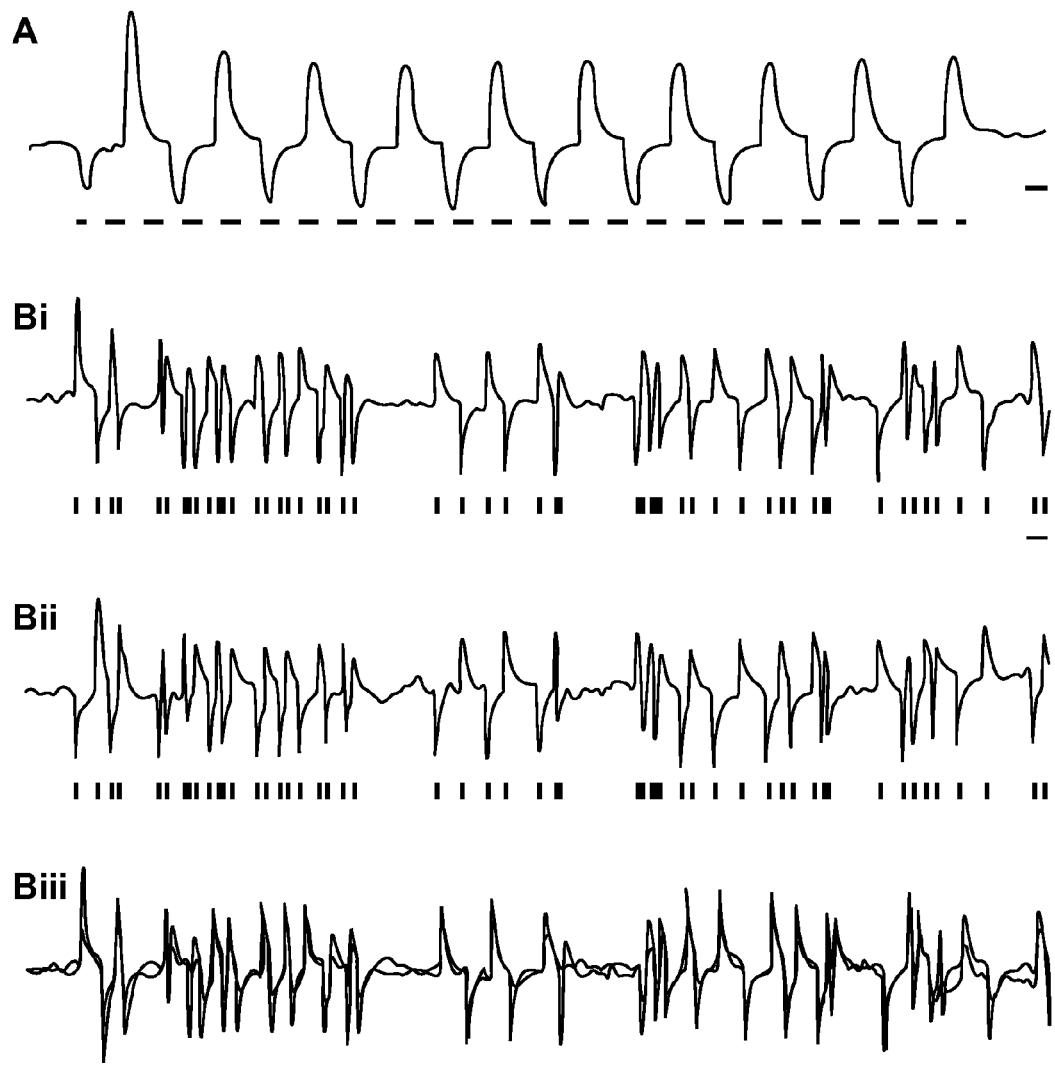
FIG. 4A shows responses of single neurons co-expressing Halo and ChR2, both under control of the CaMKII promoter, to rapidly-switched pulses of yellow and blue light, consistent with an embodiment of the present invention.
FIG. 4B shows poisson trains of rapidly-alternating yellow and blue light pulses elicited rapidly-alternating hyperpolarizations and depolarizations in the same neuron, consistent with an embodiment of the present invention.

Single neurons co-expressing Halo and ChR2, both under control of the CaMKII promoter, were implemented to allow for response to rapidly-switched pulses of yellow and blue light with hyperpolarizations and depolarizations, respectively (FIG. 4A). Poisson trains ($\lambda=100$ ms) of rapidly-alternating yellow and blue light pulses elicited rapidly-alternating hyperpolarizations and depolarizations in the same neuron (FIG. 4B). In one experiment, the same Poisson train was played back twice with the first train beginning on a blue pulse (FIG. 4Bi) and the second train beginning on a yellow pulse, (FIG. 4Bii) so that in the second trace, depolarizations were converted into hyperpolarizations and vice versa. In principle, these traces should be quite similar, but with inverted voltage scale. Indeed, FIG. 4Bii shows an inverted trace superimposed over the trace in FIG. 4Bi. The degree of superposition suggests that this approach may indeed be a viable method for high-fidelity, bi-directional control of neural activity at the millisecond timescale (FIG. 4Biii).

The inhibition provided by Halo is strong enough to silence neurons firing spikes in response to significant intracellular somatic current injections (FIG. 3), yet the photocurrents can appear and disappear within 10-15 milliseconds of light onset and offset, respectively (FIG. 1). Furthermore, the amplitude and timing of responses is reliable from trial to trial, and the amplitude of the voltage changes induced by pulses of yellow light does not detectably run down over time (FIG. 2). The use of Halo can be particularly useful for a number of reasons. For example, the timescale of inducing of and subsequent release of voltage inhibition by Halo is relatively fast.

According to another embodiment of the present invention, Halo is used without ChR2. Millisecond pulses of light can be used with Halo-expressing cells to induce hyperpolarizations of several millivolts, and therefore, may be useful for simulating background or well-timed synaptic activity. Studying the function of not only specific cell types, but specific classes of inhibitory synapse, can be accomplished by creating fusion proteins in which Halo is targeted to specific locations where inhibitory synapses uniquely cluster, such as the axon initial segment.

The ability to functionally lesion brain regions or cell types in a rapidly reversible fashion opens up a large class of experiments in which specific neuron populations must be inactivated for precise, sub-second durations during a task. ChR2, another type I opsin which obligately requires all-trans-retinal for its function, has been shown to function in slices of mammalian brain tissue, or even in the central nervous system in vivo, without needing any chemical supplementation. Therefore, it is believed that no supplementation will be needed for Halo in the intact mammalian brain and in brain slice experiments. Other labs working on classical neural model organisms such as *Drosophila* and *C. elegans* have devised ways of delivering all-trans-retinal to the nervous systems of such animals in order to enable ChR2 function, and thus, it is likely that these retinal-delivery protocols would also work for enabling Halo function in these invertebrates.

The ability to study the causal role of neural synchrony in behavior, neural computation, and neural pathology may be a particularly significant role for ChR2 and Halo, working in concert. The newly-enabled power to drive both excitation and inhibition of genetically-targeted neurons with blue and yellow light seems to be particularly valuable for probing synchrony by utilizing multiple wavelengths to perform both excitation and inhibition in the same specimen. The ability to synchronize and desynchronize neurons by balanced, yet random, patterns of excitation and inhibition may open up new horizons into understanding the causal role of neural synchrony in brain function and disease, an area of longstanding, yet growing, interest.

Optical methods for altering neural circuit function have appeal in part because in principle they can use technology developed for brain imaging. The ability to use optical fibers to image deep neural circuits, for example, also enables the stimulation of deep brain structures. Two-photon excitation methods may prove valuable for driving opsin activities, up to 1 mm deep. Another key aspect of optical methods of neural control is the speed with which activation and inactivation can take place, since it is trivial to modulate light intensity at high speeds, faster than most physiologically relevant processes. Nevertheless, non-optical and chemical approaches will continue to find many powerful uses for reliable, enduring inhibition of specific brain circuits and cell types, especially when large regions of deep brain tissue are involved.

From a neuroengineering standpoint, optical prosthetics capable of inhibiting neural activity may present less-invasive strategies for treating disorders of neural hyperactivity. ChR2 has already proven to be well-tolerated in intact mammalian neural circuits for up to a year. If Halo gains a similar track record, it is possible that Halo-enabled prosthetics may open up new horizons in controlling disorders of excitable cells, such as epilepsy, depression, neuropathic pain, and cardiac hyperexcitability. In the immediate future, the ability to study the effects of well-timed neuron or circuit inactivation in animal models of disease will rapidly reveal new principles for selecting neural circuit targets for treatment of specific disorders. There are also implications of the use of Halo in biotechnological scenarios, such as high-throughput drug screening. Several proposals (and even commercially-available systems) exist for using electrical stimulation to activate excitable cells, thus facilitating the screening of depolarization-gated ion channels. The discovery of drugs that target hyperpolarization-activated channels, such as the family of channels mediating the hyperpolarization-activated cation currents I(h) and I(f), may be useful for identifying possible drugs for tackling problems such as absence seizures, bradycardia, and other disorders. An all-optical method for screening for such drugs, which uses light of one frequency to drive inhibition, and light of another frequency to observe changes in fluorescence of an ion-sensitive chemical or genetically encoded sensor, may revolutionize this process. Thus, Halo not only presents a number of unique features that enable effective, and rapidly inducible and reversible, inhibition to be applied to a number of neural circuit questions, but may open up new horizons in biotechnology as well.

An experimental hippocampal neuron culture, transfection, and survival assay was implemented according to the following methods. Hippocampal regions CA3-CA1 of postnatal day 0 or day 1 Sprague-Dawley rats (Charles River) were isolated and treated with trypsin (1 mglml) for 12 minutes. Digestion was stopped by Hanks solution supplemented with 20% fetal bovine serum and trypsin inhibitor. Tissue was dissociated with silicone-coated Pasteur pipettes and centrifuged at 1000 rpm at 4° C. for 10 minutes. Dissociated neurons were plated on glass coverslips pre-coated with Matrigel (BD Biosciences) at a rough density of approximately two hippocampi per 24 coverslips. Neurons were transfected using a commercially available calcium phosphate transfection kit (Invitrogen), at 3-5 days in vitro. GFP fluorescence was used to identify successfully-transfected neurons, indicating a net transfection efficiency of ~7%. All images and electrophysiological recordings were made on 9-15 day-in-vitro neurons (approximately 4-10 days after transfection). Confocal images of transfected neurons were taken with a Zeiss LSM 510 confocal microscope. Cell death count was carried out on living cultures, seven days after transfection, by adding 4 µM ethidium homodimer-1 (Invitrogen) to the culture medium for 10 minutes at 37° C., then washing the cells with Tyrode's solution (see below). GFP-positive and negative neurons were counted for positive and negative ethidium fluorescence, in five regions on each of three coverslips for this viability assay.

An experiment regarding electrophysiology and optical methods was implemented according to the following methods. Whole cell patch clamp recording was made on 9-15 day-in-vitro neurons using a Multiclamp 700B amplifier, connected to a Digidata 1440 digitizer (Molecular Devices) attached to a PC running pClamp 10. During recording, neurons were bathed in Tyrode's solution containing (in mM) 138 NaCl, 2.4 KCl, 2 CaCl, 2 MgCl, 10 HEPES, 10 Glucose, 24 sucrose, 10 µM NBQX, 10 µM gabazine and 50 µM D-APV. Borosilicate glass (Warner) pipettes were filled with a solution containing (in mM) 130 K-Gluconate, 7 KCl, 2 NaCl, 1 MgCl2, 0.4 EGTA, 10 HEPES, 2 ATP-Mg, 0.3 GTP-Tris and 20 sucrose. Pipette resistance was ~6 M'Ω, and the access resistance was 10-25 M'Ω, which was monitored throughout the voltage-clamp recording. Resting membrane potential was 52-70 mV in current-clamp recording.

Photocurrents were first measured with pairs of 1-second long light pulses, separated by periods of darkness lasting 1 second, while holding neurons in voltage clamp at −70 mV, −30 mV and +10 mV to assay the properties of Halo. Light-induced membrane hyperpolarizations were induced by 1 second duration light pulses, separated by periods of 1 second darkness, in neurons current-clamped at resting membrane potential. Light pulse trains were synthesized by custom software written in MATLAB (Mathworks), and then played to the DG-4 light source through a digital-to-analog converter on the Digidata 1440. For the spike-blockade experiment, spikes were first induced via somatic current injection through the patch pipette. Most of the neurons patched easily fired action potentials with 100% probability, in response to ~300 pA current injections (4 ms duration). For each neuron, injected somatic current magnitudes guaranteed 100% firing rate of 20 spikes, at a rate of 5 Hz.

A DG-4 optical switch with 300-W xenon lamp (Sutter Instruments) was used to deliver all light pulses, for Halo or ChR2 activation. A Texas Red filter set (Chroma, excitation 560/55, diachronic 595LP, emission 645/75) was used to deliver yellow light to activate Halo. The same diachroic mirror was also used to deliver blue light, but with an excitation filter 480/40 in the DG-4, to allow ChR2 excitation. Note that the DC595LP dichroic mirror only reflects 35% of incident 460-500 nm light through the objective; custom-coated dichroics that reflect light all the way into the ultraviolet (as are available from companies such as Chroma) would be optimal.

According to one embodiment of the present invention, the survival replication, differentiation, or death of cells is modulated by electrical activity from Halo. With appropriate light pulses, Halo-expressing cells can be guided down any one of these pathways, depending on the precise pattern of stimulation used to drive activation of Halo. A specific electrical activity pattern results in a specific pattern of downstream signal transduction and in a specific cellular fate response. Therefore, targeting Halo to specific cells, then exposing them to particular light patterns, enables them to be optically driven towards survival, differentiation, replication, or death. This has many potential applications.

For example, in the case where the target cell is a stem cell, particular patterns of activity will drive the replication or differentiation of stem cells (including human embryonic stem cells), or drive the death of the stem cells (in the case where excessive replication is desired to cease). If the target cells are tumor or cancer cells, then targeting Halo to those cells will permit the use of specific and appropriate patterns of light to drive activity, and thus kill the tumor or cancer cells. If the target cells are immune cells, then silencing the cells can prevent the calcium waves that insure cell survival, and reduce the prevalence of autoimmune disease.

Other target cells of this kind may include secretory or organ cells or their precursors, cardiac or other muscle cells, or glial cells in the brain. In each of these cases, it is desirable to control the replication, differentiation, and death of these cells precisely. Halo will be useful for controlling these things in vitro, in vivo in experimental animals, or in vivo in humans (before or after transplantation into the body)—wherever light can be delivered, such as through the skin, via small LEDs, or lasers, or through optical fibers or thin optical endoscopes.

Screening for drugs that modulate ion channel function (e.g., blocking or facilitating ion channel function) can be accomplished using Halo to screen for drugs that modulate ion channel function. One embodiment involves one or more of the following steps:
1) stably express Halo in a cell line;
2) stably express an ion channel of interest ("channel n") in the same cell line;
3) label the cells with a voltage sensitive dye (or other indicator, see below);
4) expose said cells to light, and record the fluorescence of the voltage sensitive dye;
5) expose said cells to a candidate compound that monitors the function of channel n; and
6) expose said cells to light a second time, and record the fluorescence of the voltage sensitive dye.

If the fluorescence is greater during step 6) than step 4), then the candidate drug facilitates channel function. If the fluorescence is smaller during step 6) than step 4), then the candidate drug diminishes channel function. If the fluorescence is equal in steps 4) and 6) (allowing for any bleaching of the dye), then the drug does not affect channel function. In this way, drugs that affect channel function can be detected extremely rapidly.

Steps 1) and 2) of the above process may take several hours or days, but the resulting cell line then suffices for the screening of many (perhaps millions of) drugs, which modulate channel n. Steps 3), 4), 5), and 6) take only a few seconds each; preferably, steps 4), 5), and 6) each take less than 1 second. Steps 4), 5), and 6) take place in a robotic device that moves a 96- or 384-well plate into the focus of an optical beam (see the last section for details on devices). The wells of the plate would all contain the same cell line, in order to facilitate the screening of drugs that affect a particular channel, or each well would contain cells of a different cell line, in order to facilitate the screening of one drug against many different channels ("screening against side effects," see below).

Step 3 can include the use of a voltage-sensitive dye for fast kinetics; however, another dye (e.g., a calcium-sensitive dye in the case that channel n is a calcium channel) could also serve to indicate whether channel function is modulated by the drug. Genetically encoded indicators of voltage or calcium would also be useful for reading out the activity of the cell (e.g., FLASH, GCaMP2, cameleon, etc.). In this case, these indicators would be stably expressed in the cell line as well. Other methods of reading out whether the drug had an effect could also be useful for supplementing this readout (e.g., immunostaining for the phosphorylation of a site that is phosphorylated during or after periods of ion channel activity).

Blindness and other sensory deficits affect millions of people worldwide, severely impacting their quality of life. Halo can be targeted to somatic cells in the human patient to provide a type of sensory prostheses. For example, some forms of blindness destroy photosensor function but leave signal processing in downstream neurons intact. In such diseases, such as macular degeneration or retinitis pigmentosa, targeting Halo to the "off" retinal ganglion cells (e.g., by injecting viruses expressing Halo into the retinal cell layers inside the eye) would enable restoration of visual function. As light increases in the environment, Halo would inhibit the "off" cells, causing increased visual responses in the brain. In such patients treated with Halo targeted to retinal ganglion cells, the retinal ganglion cells would themselves become photosensitive, enabling vision with resolution comparable to the native eye, and not requiring invasive technology beyond that point. Halo is sufficiently sensitive to detect sunlight (power ~1 kW/m^2), with maximal sensitivity in the part of the spectrum that is greatest in sunlight. Expressing Halo in a retinal cell, accompanied with a projection device that would amplify the ambient light, would enable vision inside or in lowlight conditions.

Another implementation of Halo involves situations where the central nervous system neurons in a person are infected with virus expressing Halo (or otherwise come to express Halo). These neurons would then be inhibitable by pulses of yellow light. This gene therapy approach would therefore allow optical inhibition of precise neuronal targets in the brain. If the targeted neurons are epileptic, this would enable silencing of those cells without needing ablative surgery. If the targeted neurons were in the frontal cortex or other parts of the brain, these light-sensitive neurons would permit optical modulation of emotion or cognition. If the targeted neurons were in the spinal cord, neurons that mediate pain stimuli could then be inhibited by light.

In general, such a gene therapy approach opens up a new kind of generalized prosthetic in defined parts of the nervous system. The prosthetic allows light to be converted into neural activity.

In another instance, Halo is targeted to specific and different parts of a cell. For example, targeting Halo to the axon hillock using the AIS (axon initial segment) targeting sequence allows more powerful inhibition. Fusing Halo to a targeting sequence of DNA, so that the resultant protein contains both Halo and the targeting peptide, allows Halo to be sent to the presynaptic terminal, the postsynaptic terminal, the nucleus, or other intracellular compartments. Such targeting sequences include PDZ domains, glutamate and GABA receptor C-terminal sequences, ion channel C-terminal sequences, presynaptic scaffolding targeting sequences, and other targeting sequences. These versions of Halo can then be used to trigger specific intracellular signaling events, including those important for neuroprotection, memory, or other enduring signaling functions.

In a combinatorial fashion, these reagents could complement the other applications of Halo. For example, these reagents could be useful for drug screening (e.g., finding drugs that modulate the function of a channel in a particular subcellular compartment). These reagents could also be useful for prosthetic devices (e.g., driving activity on the dendrites of a neuron, to more closely mimic natural synaptic activity).

Various embodiments, including but not limited to those involving drug screening, employ an optical imaging device containing 1) a light source (LED, lamp, laser) for illuminating the cell expressing Halo and driving a change in cell voltage, 2) a light source for illuminating a dye or indicator, possibly the same light source as used for driving the voltage change, and 3) a switch for alternating between the two light sources or a beamsplitter for simultaneous non-interfering delivery of both kinds of light. The fluorescence of the dye or indicator would be measured by a sensor (CCD camera, PMT, or photodiode). This kind of device can be useful for ion channel drug screening, as described above. The device itself consists of a robotic arm for moving a plate (e.g., a 384-well plate) through the arena where the light sources and sensor are present.

In one embodiment, diagnostic applications, as mentioned herein, use a combined light source imaging device. For example, taking cells from a patient, expressing Halo in them, and then exposing them to light, can be used to reveal patient-specific ion channel syndromes in biopsy samples or in cells of the circulatory system.

For various implementations, an implantable or head-mounted LED, or other small light source can be used. Such a light source can be implanted under the skin, under the skull, deep within the brain, or deep within another organ of interest, in which Halo-expressing cells are also located (either exogenously introduced, or endogenously located and targeted with a virus). This device can be used for stimulating Halo in cells located directly adjacent to the light source. A strip of LEDs, each individually controllable, is useful. For the example of the cortical implant, a 2-dimensional array of LEDs is useful.

For medical applications, various embodiments have LEDs that are remotely powered. A remotely-powered LED can be made, for example, by combining an LED in a closed-loop series circuit with an inductor. This would allow radiofrequency (RF) energy or rapidly changing magnetic fields (e.g., delivered by a transcranial magnetic resonance (TMS) coil) to temporarily power-up the inductor, and thus the connected LED, allowing local delivery of light, even deep in a brain structure. In certain embodiments, such a device is implanted under the skin, under the skull, deep within the brain, or deep within another organ of interest in which Halo-expressing cells are also located (either exogenously introduced, or endogenously located and targeted with a virus). Optionally, another device is used to remotely deliver RF or magnetic energy (e.g., placed nearby or worn on the patient) for activating the implanted device.

N. pharaonis halorhodopsin with mammalian-optimized codon usage was synthesized as a DNA sequence according to the sequence listing provided on the following page as Sequence Listing A.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include the use of digital logic or microprocessors to control the emitted light. Such modifications and changes do not depart from the true spirit and scope of the present invention, which is set forth in the following claims.

SEQUENCE LISTING A

The N. pharaonis halorhodpsin with mammalian-optimized codon usage was synthesized according to the following DNA sequence (876 base pairs).

ATGACTGAGACCCTCCCACCCGTGACTGAAAGCGCCGTCGCTCTGCAAGC

AGAGGTTACCCAGCGGGAGCTGTTCGAGTTCGTCCTCAACGACCCCCTCC

TGGCTTCTAGCCTCTACATCAACATTGCTCTGGCAGGCCTGTCTATACTG

CTGTTCGTCTTCATGACCAGGGGACTCGATGACCCTAGGGCTAAACTGAT

TGCAGTGAGCACAATTCTGGTTCCCGTGGTCTCTATCGCTTCCTACACTG

GGCTGGCATCTGGTCTCACAATCAGTGTCCTGGAAATGCCAGCTGGCCAC

TTTGCCGAAGGGAGTTCTGTCATGCTGGGAGGCGAAGAGGTCGATGGGGT

TGTCACAATGTGGGGTCGCTACCTCACCTGGGCTCTCAGTACCCCCATGA

TCCTGCTGGCACTCGGACTCCTGGCCGGAAGTAACGCCACCAAACTCTTC

ACTGCTATTACATTCGATATCGCCATGTGCGTGACCGGGCTCGCAGCTGC

CCTCACCACCAGCAGCCATCTGATGAGATGGTTTTGGTATGCCATCTCTT

GTGCCTGCTTTCTGGTGGTGCTGTATATCCTGCTGGTGGAGTGGGCTCAG

GATGCCAAGGCTGCAGGGACAGCCGACATGTTTAATACACTGAAGCTGCT

CACTGTGGTGATGTGGCTGGGTTACCCTATCGTTTGGGCACTCGGCGTGG

AGGGAATCGCAGTTCTGCCTGTTGGTGTGACAAGCTGGGGCTACTCCTTC

CTGGACATTGTGGCCAAGTATATTTTTGCCTTTCTGCTGCTGAATTATCT

GACTTCCAATGAGTCCGTGGTGTCCGGCTCCATACTGGACGTGCCATCCG

CCAGCGGCACACCTGCCGATGACTGA).

The Halo-GFP fusion protein was generated by PCR amplification of the Halo gene with primers 5'GAATTCGC-CACCATGACTGAGACCCTCCCACCCGTG and 3'GGATCCGTCATCGGCAGGTGTGCCGCTGGC and inserted into the EcoRI and BamHI cites of pEGFP-N3 (Clontech), which has the CMV promoter. The Halo-GFP fusion protein sequence was then PCR amplified with primers 5'CCGGTGCCACCATGACTGAGACCCTC-CCACCCGTG and 3'GAATTCTTACTTGTA-CAGCTCGTCCATCGG and inserted into lentiviral vector FCK(1.3)GW containing the CaMKII promoter via AgeI and EcoRI sites. All constructs were verified by sequencing. The channelrhodopsin construct used in various experiments, FCK-hCmC, contains the human/mammalian codon-optimized gene ChR2 fused to fluorescent protein mCherry, under the CaMKII promoter.

What is claimed is:

1. A method for optical stimulation of a mammalian cell expressing a light-driven chloride ion pump from *Natronobacterium pharaonis* (NpHR), the method comprising:
   providing a sequence of optical or electrical stimuli to the cell, each stimulus increasing the probability of a depolarization event occurring in the cell; and
   exposing the mammalian cell to yellow light to activate the expressed NpHR ion pump, thereby decreasing the probability of depolarization events occurring in the cell.

2. The method of claim 1, wherein the optical light has a wavelength of around 560 nm.

3. The method of claim 1, wherein the optical light is about 10 mW/mm$^2$.

4. The method of claim 1, wherein sequence of stimuli to the cell is a sequence of electrical pulses.

5. The method of claim 1, wherein the cell also expresses a Channelrhodopsin 2 ion channel and the sequence of stimuli to the cell is a sequence of optical pulses.

6. The method of claim 1, wherein the cell is stimulated in vitro.

7. The method of claim 1, wherein the cell is stimulated in vivo.

8. The method of claim 1, wherein the cell is a neuron.

9. The method of claim 1, wherein the NpHR ion pump is encoded by a mammalian codon-optimized nucleotide sequence.

10. The method of claim 1, wherein the NpHR ion pump is encoded by a nucleotide sequence that is operably linked to a CaMKII promoter.

* * * * *

SEQUENCE LISTING

<160> NUMBER OF SEQ ID NOS: 5

<210> SEQ ID NO 1
<211> LENGTH: 876
<212> TYPE: DNA
<213> ORGANISM: Artificial Sequence
<220> FEATURE:
<223> OTHER INFORMATION: mammalian codon-optimized sequence from
      Natronobacterium pharaonis

<400> SEQUENCE: 1
atgactgaga ccctcccacc cgtgactgaa agcgccgtcg ctctgcaagc agaggttacc    60

-continued

| | |
|---|---|
| cagcgggagc tgttcgagtt cgtcctcaac gacccctcc tggcttctag cctctacatc | 120 |
| aacattgctc tggcaggcct gtctatactg ctgttcgtct tcatgaccag gggactcgat | 180 |
| gaccctaggg ctaaactgat tgcagtgagc acaattctgg ttcccgtggt ctctatcgct | 240 |
| tcctacactg ggctggcatc tggtctcaca atcagtgtcc tggaaatgcc agctggccac | 300 |
| tttgccgaag ggagttctgt catgctggga ggcgaagagg tcgatggggt tgtcacaatg | 360 |
| tggggtcgct acctcacctg gctctcagt accccatga tcctgctggc actcggactc | 420 |
| ctggccggaa gtaacgccac caaactcttc actgctatta cattcgatat cgccatgtgc | 480 |
| gtgaccgggc tcgcagctgc cctcaccacc agcagccatc tgatgagatg gttttggtat | 540 |
| gccatctctt gtgcctgctt tctggtggtg ctgtatatcc tgctggtgga gtgggctcag | 600 |
| gatgccaagg ctgcagggac agccgacatg tttaatacac tgaagctgct cactgtggtg | 660 |
| atgtggctgg gttaccctat cgtttgggca ctcggcgtgg agggaatcgc agttctgcct | 720 |
| gttggtgtga caagctgggg ctactccttc ctggacattg tggccaagta tattttgcc | 780 |
| tttctgctgc tgaattatct gacttccaat gagtccgtgg tgtccggctc catactggac | 840 |
| gtgccatccg ccagcggcac acctgccgat gactga | 876 |

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2

| | |
|---|---|
| gaattcgcca ccatgactga gaccctccca cccgtg | 36 |

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3

| | |
|---|---|
| ggatccgtca tcggcaggtg tgccgctggc | 30 |

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4

| | |
|---|---|
| ccggtgccac catgactgag accctcccac ccgtg | 35 |

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5

| | |
|---|---|
| gaattcttac ttgtacagct cgtccatcgg | 30 |